United States Patent

Fuerst et al.

(10) Patent No.: US 8,426,646 B2
(45) Date of Patent: Apr. 23, 2013

(54) PROCESS FOR THE PRODUCTION OF AMINES

(75) Inventors: Maren Fuerst, Muenchwilen (CH); Thomas Vettiger, Muenchwilen (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 369 days.

(21) Appl. No.: 12/668,053

(22) PCT Filed: Jun. 30, 2008

(86) PCT No.: PCT/EP2008/005338
§ 371 (c)(1),
(2), (4) Date: May 24, 2010

(87) PCT Pub. No.: WO2009/007033
PCT Pub. Date: Jan. 15, 2009

(65) Prior Publication Data
US 2010/0228055 A1    Sep. 9, 2010

(30) Foreign Application Priority Data

Jul. 12, 2007  (EP) .................................... 07013664

(51) Int. Cl.
*C07C 211/00* (2006.01)
*C07C 209/00* (2006.01)

(52) U.S. Cl.
USPC ............ 564/407; 564/404; 564/405; 564/307

(58) Field of Classification Search .................. None
See application file for complete search history.

(56) References Cited

U.S. PATENT DOCUMENTS 7,737,301 B2 * 6/2010 Walter et al. ................. 564/307
7,951,752 B2 * 5/2011 Ehrenfreund et al. ........ 504/239

FOREIGN PATENT DOCUMENTS
WO    2007025693    3/2007

OTHER PUBLICATIONS

Artamkina et al., Tetrahedron Letters (2001), 42(26), 4381-4384.*

* cited by examiner

*Primary Examiner* — Karl J Puttlitz
(74) *Attorney, Agent, or Firm* — R. Kody Jones

(57) ABSTRACT

The present invention relates to a process for the preparation of compounds of formula (I) wherein $R_1$ is $C_6$-$C_7$ alkyl or a group ($A_1$) wherein $R_2$, $R_3$ and $R_4$ are each independently of the others hydrogen or $C_1$-$C_4$ alkyl; wherein a compound of formula (II) wherein $R_1$ is as defined for formula (I) and X is bromine or chlorine, is reacted with urea in the presence of a base and a catalytic amount of at least one palladium complex compound, wherein the palladium complex compound comprises at least one ferrocenyl-biphosphine ligand.

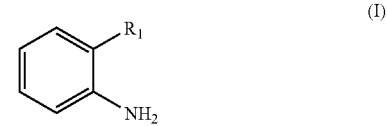

(I)

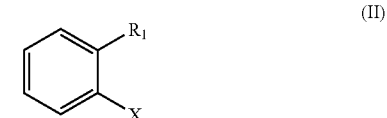

(II)

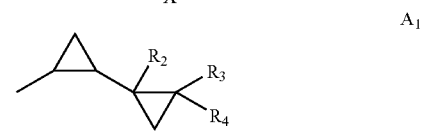

$A_1$

6 Claims, No Drawings

PROCESS FOR THE PRODUCTION OF AMINES

This application is a 371 of International Application No. PCT/EP2008/005338 filed Jun. 30, 2008, which claims priority to EP 07013664.3 filed Jul. 12, 2007, the contents of which are incorporated herein by reference.

The present invention relates to a process for the amination of ortho-bicyclopropyl-substituted or ortho-$C_6$-$C_7$alkyl-substituted halobenzenes.

Ortho-bicyclopropyl- or ortho-$C_6$-$C_7$alkyl-substituted primary anilines, such as, for example, 2-bicyclopropyl-2-yl-phenylamine and 2-(1,3-dimethyl-butyl)-phenylamine are valuable intermediates for the preparation of fungicides such as those described, for example, in WO 03/74491 and WO 03/10149. Agrochemicals are generally produced in large quantities. For example the fungicide chlorothalonil has been produced in the year 2005 in a quantity of over 23,000 metric tons.

In general terms, anilines with sterically less demanding ortho-substituents, such as the ortho-tolyl-amine, can be prepared from the reactions of halobenzenes with ammonia by means of palladium-catalysed cross-coupling as described in Journal of the American Chemical Society, 128, 10028-10029, 2006. But the successful use of palladium-containing catalysts in a one-step amination of more sterically hindered halobenzenes, such as ortho-bicyclopropyl- or ortho-$C_6$-$C_7$alkyl-substituted halobenzenes has not been described.

Attempts to prepare ortho-tolyl-anilines by the reaction of halobenzenes with urea by means of palladium-catalysed cross-coupling have been unsuccessful as the main product has been the dimer (see Russian Journal of Organic Chemistry, 42, 1683-1689, 2006).

According to WO 03/74491, ortho-bicyclopropyl-substituted primary anilines can be prepared by reacting the corresponding ortho-bicyclopropyl-substituted halobenzenes in a two-step reaction first with benzophenone-imine in a palladium-catalysed reaction and then reacting the reaction products with hydroxylamine hydrochloride and sodium acetate or with acids, for example hydrochloric acid. Such a reaction procedure is unsuitable for the large-scale production of ortho-bicyclopropyl-substituted primary anilines, however, on account of the need for a second process step and the relative high cost of the benzophenone-imine. Furthermore, the reaction procedure is described in WO 03/74491 exclusively for bromo- or iodo-benzenes, not for chlorobenzenes. It has been found that the reaction procedure described in WO 03/74491 is poorly suited to the imination of the less reactive but more economically priced 2-(2-chlorophenyl)-bicyclopropanes in high yields.

According to WO 07/25693, ortho-bicyclopropyl-substituted primary anilines can be prepared by reacting the corresponding ortho-bicyclopropyl-substituted halobenzenes in a two-step reaction first with benzylamine in a palladium(II)-catalysed reaction and then hydrogenating the reaction products with, for example hydrogen in the presence of a Pd/C-catalyst. The application of such a reaction procedure to large-scale production is associated with high costs on account of the need for a second process step.

A successful one-step-amination of the sterically hindered ortho-bicyclopropyl-substituted halobenzenes using copper-containing catalysts is described in WO 06/61226. But such a reaction procedure is again not attractive for large-scale production due to the high cost for copper-salt waste management. Furthermore, it has been found that the reaction procedure described in WO 06/61226 is poorly suited for an amination of the less reactive but more economically priced 2-(2-chlorophenyl)bicyclopropanes in high yields.

The problem of the present invention is accordingly to provide a new process for the preparation of ortho-bicyclopropyl-substituted primary anilines which avoids the above-mentioned disadvantages of the known process and makes it possible to prepare these compounds at economically reasonable cost and in easily manageable manner in high yields and good quality.

The present invention accordingly relates to a process for the preparation of compounds of formula I

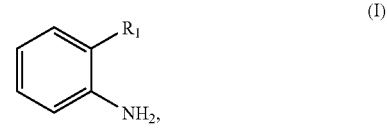

(I)

wherein $R_1$ is $C_6$-$C_7$alkyl or a group $A_1$

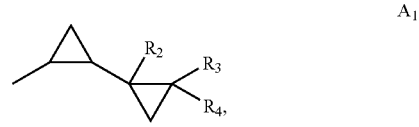

$A_1$ wherein $R_2$, $R_3$ and $R_4$ are each independently of the others hydrogen or $C_1$-$C_4$ alkyl;
wherein a compound of formula II

(II)

wherein $R_1$ is as defined for formula I and X is bromine or chlorine, is reacted with urea in the presence of a base and a catalytic amount of at least one palladium complex compound, wherein the palladium complex compound comprises at least one ferrocenyl-biphosphine ligand.

Compounds of formula I may occur in various stereoisomeric forms. The process according to the invention includes the preparation of said individual stereoisomeric forms and the preparation of mixtures of said stereoisomeric forms in any ratio.

The process according to the invention is suitable preferably for the preparation of compounds of formula I, wherein $R_1$ is $A_1$, $R_2$ is hydrogen or $C_1$-$C_4$alkyl and $R_3$ and $R_4$ are hydrogen; preferably $R_2$ is hydrogen or methyl and $R_3$ and $R_4$ are hydrogen. The process according to the invention is suitable especially for the preparation of compounds of formula IA

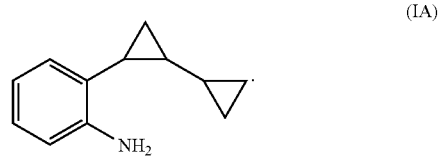 [SMILES: Nc1ccccc1C1CC1C1CC1]

(IA)

The process according to the invention is suitable preferably for the preparation of compounds of formula I wherein $R_1$ is 1,3-dimethyl-butyl or 1,3,3-trimethyl-butyl; preferably 1,3-dimethyl-butyl.

Compounds of formula II wherein X is chlorine are preferably used in the process according to the invention. Compounds of formula II wherein X is bromine are preferably used in the process according to the invention.

In the process according to the invention compounds of formula II can be used typically in concentrations of between 0.01 M and 5 M. More preferably, compounds of formula II are used in concentrations of between 0.1 M and 5 M. Even more preferably, compounds of formula II are used in concentrations of between 0.1 M and 2 M. The possibility of using high concentrations of compounds of formula II is an important advantage of the process according to the invention as with high concentrations of starting material less solvent is needed, which makes the process according to the invention especially suitable for large-scale production.

The palladium complex compounds which are used in the process according to the invention are formed from a palladium precursor and at least one ferrocenyl-biphosphine ligand. In the process according to the invention, the palladium complex compounds are preferably present in dissolved form as palladium-ligand complexes.

The palladium complex compounds may be used as already formed palladium complex compounds in the process according to the invention or are formed in situ in the process according to the invention.

In order to form palladium complex compounds, a palladium precursor is reacted with at least one ferrocenyl-biphosphine ligand. In the event of incomplete reaction, it can be the case that minor amounts of palladium precursor or of ligand do not dissolve in the reaction mixture.

Suitable palladium precursors are palladium acetate, palladium dichloride, palladium dichloride solution, palladium$_2$(dibenzylidene-acetone)$_3$ or palladium (dibenzylidene-acetone)$_2$, palladium tetrakis(triphenylphosphine), palladium-on-carbon, palladium dichlorobis(benzonitrile), palladium (tris-tert-butylphosphine)$_2$ or a mixture of palladium$_2$(dibenzylidene-acetone)$_3$ and palladium (tris-tert-butylphosphine)$_2$.

Ferrocenyl-biphosphine ligands are bidentate tertiary phosphine ligands commonly used in palladium-catalyzed reactions. Such bidentate ligands occupy two coordination sites and hence are able to chelate the palladium species.

Suitable ferrocenyl-biphosphine ligands are:

(R)-(−)-1-[(S)-2-(dicyclohexylphosphino)ferrocenyl]ethyldi-tert-butylphosphine

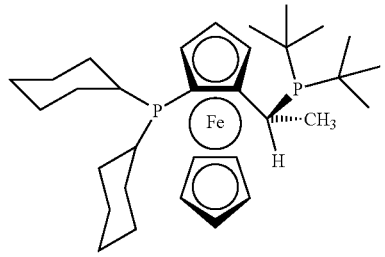

1,1'-bis(diphenylphosphino)ferrocene (dppf), 1,1'-bis(di-tert-butylphosphino)-ferrocene, (R)-(−)-1-[(S)-2-(bis(4-trifluoromethylphenyl)phosphino)ferrocenyl]ethyl-di-tert-butyl-phosphine, (R)-(−)-1-[(S)-2-(di(3,5-bis-trifluoromethylphenyl)phosphino)ferrocenyl]ethyl-dicyclohexylphosphine, (R)-(−)-1-[(S)-2-(di(3,5-bis-trifluoromethylphenyl)phosphino)ferrocenyl]ethyldi(3,5-dimethylphenyl)phosphine, (R)-(−)-1-[(S)-2-(dicyclohexylphosphino)ferrocenyl]ethyldicyclohexylphosphine, (S)-(+)-1-[(R)-2-(dicyclohexylphosphino)ferrocenyl]ethyldicyclohexylphosphine, (S)-(+)-1-[(R)-2-(dicyclohexylphosphino)ferrocenyl]ethyldiphenylphosphine, (R)-(−)-1-[(S)-2-(bis(3,5-dimethyl-4-methoxyphenyl)phosphino)ferrocenyl]ethyldicyclohexylphosphine, (S)-(+)-1-[(R)-2-(difurylphosphino)ferrocenyl]ethyldi-3,5-xylylphosphine, (R)-(−)-1-[(S)-2-(diphenylphosphino)ferrocenyl]ethyldi-tert-butylphosphine, (S)-(+)-1-[(R)-2-(diphenylphosphino)ferrocenyl]ethyldi-tert-butylphosphine, (R)-(−)-1-[(S)-2-(diphenylphosphino)ferrocenyl]ethyldicyclohexylphosphine, (R)-(+)-1-[(R)-2-(diphenylphosphino)ferrocenyl]ethyldicyclohexylphosphine, (S)-(+)-1-[(R)-2-(diphenylphosphino)-ferrocenyl]ethyldicyclohexylphosphine, (R)-(−)-1-[(S)-2-(dicyclohexylphosphino)ferrocenyl]ethyldiphenylphosphine, (R)-(−)-1-[(S)-2-(diphenyl)phosphino)ferrocenyl]ethyldi(3,5-dimethylphenyl)phosphine, (R)-(−)-1-[(S)-2-(di-tert-butyl-phosphino)ferrocenyl]ethyl-di-o-tolylphosphine

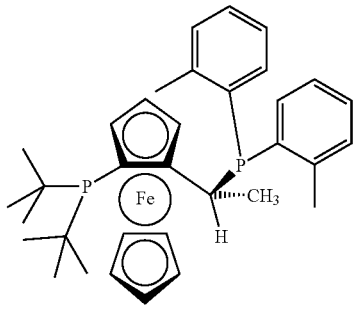

(R)-(−)-1-[(S)-2-(bis(3,5-dimethyl-4-methoxyphenyl)phosphino)ferrocenyl]-ethyl-di-tert-butylphosphine

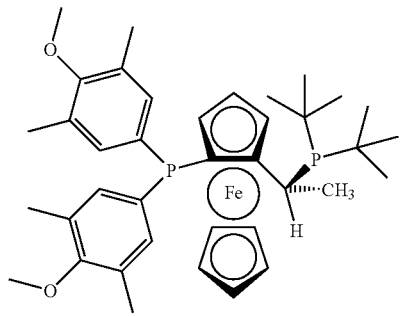

(R)-(−)-1-[(S)-2-(diethylphosphino)ferrocenyl]-
ethyl-di-tert-butylphosphine

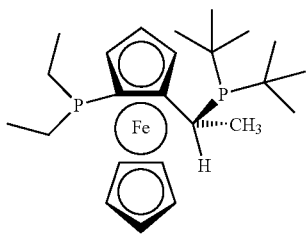

(R)-(−)-1-[(S)-2-(P-methyl-P-isopropyl-phosphino)
ferrocenyl]ethyldicyclohexylphosphine

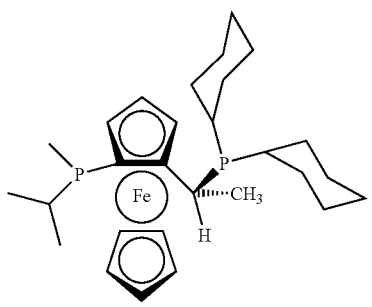

(R)-(−)-1-[(S)-2-(P-methyl-P-phenyl-phosphino)
ferrocenyl]ethyl-di-tert-butylphosphine

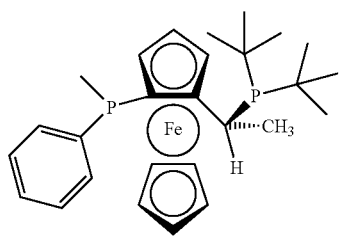

and racemic mixtures thereof, especially racemic mixtures of 1-[2-(di-tert-butylphosphino)ferrocenyl]ethyl-di-o-tolylphosphine, 1-[2-(dicyclohexylphosphino)-ferrocenyl] ethyldi-tert-butylphosphine and 1-[2-(diphenylphosphino) ferrocenyl]ethyldicyclohexylphosphine.

One palladium complex compound or a mixture of palladium complex compounds may be used in the process according to the invention.

For formation of the palladium complex compound, preference is given to the use, as palladium precursor, of palladium acetate, palladium$_2$ (dibenzylidene-acetone)$_3$, palladium (dibenzylidene-acetone)$_2$, palladium dichloride solution, palladium dichloride or a mixture of palladium$_2$ (dibenzylidene-acetone)$_3$ and palladium (tris-tert-butylphosphine)$_2$. Special preference is given to the use of palladium acetate or palladium dichloride.

Suitably, the palladium acetate is trimeric palladium acetate.

At least one ligand is used for formation of the palladium complex compound.

Preference is given to the use of palladium complex compounds which comprise at least one ligand selected from (R)-(−)-1-[(S)-2-(dicyclohexylphosphino)ferrocenyl]ethyldi-tert-butylphosphine and racemic 1-[2-(dicyclohexylphosphino)ferrocenyl]ethyldi-tert-butylphosphine.

Preference is given to the use of palladium complex compounds which comprise racemic 1-[2-(dicyclohexylphosphino)ferrocenyl]ethyldi-tert-butylphosphine.

Palladium complex compounds, palladium precursors and/or ligands are used in catalytic amounts in the process according to the invention.

Palladium complex compounds are used preferably in a ratio of from 1:10 to 1:10 000 relative to compounds of formula II, especially in a ratio of from 1:50 to 1:100.

Palladium precursors are used preferably in a ratio of from 1:10 to 1:10 000 relative to compounds of formula II, especially in a ratio of from 1:50 to 1:500.

Ligands are used preferably in a ratio of from 1:10 to 1:10 000 relative to compounds of formula II, especially in a ratio of from 1:50 to 1:100.

Suitable bases are, for example, alcoholates, e.g. sodium tert-butanolate (also known as sodium tert butoxide), potassium tert-butanolate (also known as potassium tert butoxide), sodium methanolate (also known as sodium methoxide) or sodium ethanolate (also known as sodium ethoxide), or inorganic bases such as carbonates, e.g. $K_2CO_3$, $Na_2CO_3$ or $Cs_2CO_3$, hydroxides, e.g. NaOH or KOH, phosphates, e.g. $K_3PO_4$; in one embodiment, preference is given to alcoholates and special preference is given to sodium tert-butanolate.

When NaOH or KOH is used as the base, a phase transfer catalyst such as, for example, cetyltrimethylammonium bromide or crown ethers may be used.

Suitable amounts of base for this reaction are, for example, from 1 to 6 equivalents, especially from 1 to 2 equivalents.

The reaction according to the invention may be carried out in an inert solvent, optionally diluted with water.

In one embodiment of the invention, the reaction according to the invention is carried out in an inert solvent. Suitable solvents are, for example, a compound of formula V

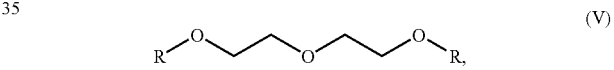

(V)

wherein R is $C_1$-$C_6$ alkyl, preferably methyl; an ether solvent, such as dimethoxyethane; tert-butyl methyl ether; tetrahydrofuran; dioxane; diethyleneglycoldiethylether or anisole; a sulfone solvent, such as sulfolane; an amide solvent, such as N-methylpyrrolidone or dimethylacetamide; or an aromatic hydrocarbon solvents, such as toluene; xylene or trimethylbenzenes such as, for example, mesitylene; and also mixtures of said solvents. Preferred solvents are ether solvents and amide solvents. In one embodiment, the solvent is an amide solvent, more preferably N-methylpyrrolidone. In another embodiment, the solvent is an ether solvent, more preferably diethyleneglycoldiethylether.

In one embodiment, the inert solvent is anhydrous and preferentially degassed.

The reaction according to the invention is carried out at ambient temperature or at elevated temperature, preferably in a temperature range from 50° C. to 180° C., especially in a temperature range from 50° C. to 140° C.

The reaction according to the invention can be carried out at normal pressure, but not limited to.

The reaction time of the reaction according to the invention is generally from 0.5 to 48 hours, preferably from 1 to 30 hours, especially from 1 to 18 hours.

The reaction according to the invention may be carried out in an inert gas atmosphere. For example, nitrogen or argon is used as inert gas.

In the reactions according to the invention, urea is typically used in equimolar amounts or in excess relative to compounds of formula II, preferably in an up to 10-fold excess, especially in an up to 5-fold excess, more especially in an 1.3-fold to 2-fold excess.

The compounds of formula II are generally known and can be prepared according to the processes described in WO 03/74491, WO 03/10149 and WO 07/25693.

Palladium complex compounds, palladium precursors and ligands as used in the process according to the invention are generally known and, for the most part, commercially available.

The present invention will be explained in greater detail using the following Examples:

EXAMPLE P1

Preparation of 2-bis-cyclopropylaniline (Compound A1)

In an argon atmosphere 811 mg 2-(2-chlorophenyl)bicyclopropyl, 18 mg palladium acetate (trimer), 43 mg (R)-(−)-1-[(S)-2-(dicyclohexylphosphino)ferrocenyl]ethyldi-tert-butylphosphine, 365 mg urea, 2.4 g sodium tert-butanolate in 4 ml degassed N-methylpyrrolidone were stirred at elevated temperature at 134° C. for 5 h.

The content/purity of 2-biscyclopropylaniline (compound A1) in the reaction mixture was determined by gas chromatography. 79.9% (area GC) of 2-biscyclopropylaniline was detected; with 1.3% (area GC) of starting material and 6.7% (area GC) of dimeric by-product and 2.9% (area GC) of dehalogenated by-product.

The reaction was quenched with water, diluted with N-methylpyrrolidone and extracted three times with toluene. The organic solvent was removed in vacuo. The crude product was purified by chromatography over silicagel (hexane:ethylacetate 10/1 with addition of 1% (v/v) triethylamine). 496 mg (68% of theory) of 2-biscyclopropylaniline were obtained in the form of a slightly orange liquid, the product was characterized by NMR.

EXAMPLE P2

Preparation of 2-bis-cyclopropylaniline (Compound A1)

In an argon atmosphere 865 mg 2-(2-chlorophenyl)bicyclopropyl, 18 mg palladium acetate (trimer), 46 mg (R)-(−)-1-[(S)-2-(dicyclohexylphosphino)ferrocenyl]ethyldi-tert-butylphosphine, 363 mg urea, 2.4 g sodium tert-butanolate in 8 ml degassed diethylengylcoldiethylether were stirred at elevated temperature at 144° C. for 5 h.

The content/purity of 2-biscyclopropylaniline (compound A1) in the reaction mixture was determined by gas chromatography. 70.7% (area GC) of 2-biscyclopropylaniline was detected; with 19% (area GC) of dimeric by-product and 9% (area GC) of dehalogenated by-product.

Using the above Examples, the following compounds of formula I can be prepared:

TABLE 1

Compounds of formula I

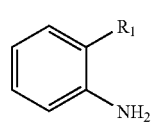
(I)

| Comp. no. | $R_1$ | $R_2$ | $R_3$ | $R_4$ |
|---|---|---|---|---|
| A1 | $A_1$ | H | H | H |
| A2 | $A_1$ | H | $CH_3$ | H |

TABLE 1-continued

Compounds of formula I

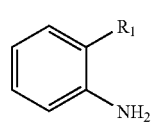
(I)

| Comp. no. | $R_1$ | $R_2$ | $R_3$ | $R_4$ |
|---|---|---|---|---|
| A3 | 1,3-dimethyl-butyl | — | — | — |
| A4 | 1,3,3-trimethyl-butyl | — | — | — |

As a result of the provision of the present invention, it is possible to aminate ortho-bicyclopropyl- or ortho-$C_6$-$C_7$alkyl-substituted halobenzenes in high yields and with little outlay.

The starting compounds of the process of the present invention are distinguished by being readily accessible and easily handled and, in addition, they are economically priced.

In a preferred embodiment of the process according to the invention, the palladium and/or the palladium complex compound used in the process is recycled. This embodiment constitutes a variant of the process according to the invention which is especially interesting from an economic point of view.

In a preferred embodiment of the invention, compounds of formula II wherein X is chlorine are used. The starting compounds of this preferred embodiment of the process of the invention are distinguished by being especially readily accessible and economical. It is known, however, that, under the conditions of palladium-catalysed cross-coupling, this class of starting compounds, the sterically hindered, deactivated, at least ortho-substituted chlorobenzene substrates, are especially difficult to aminate because of the extremely low reactivity of the chlorine leaving group, compared to bromobenzene substrates. As this embodiment of the invention makes those starting compounds accessible to the palladium-catalysed cross-coupling, this embodiment accordingly constitutes a variant of the process according to the invention, which is especially interesting from an economic point of view.

What is claimed is:

1. A process for the preparation of compounds of formula I

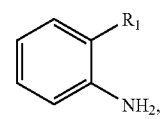
(I)

wherein $R_1$ is $C_6$-$C_7$ alkyl or a group $A_1$

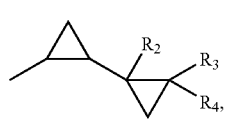
$A_1$ wherein $R_2$, $R_3$ and $R_4$ are each independently of the others hydrogen or $C_1$-$C_4$ alkyl;
wherein a compound of formula II

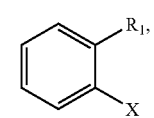
(II)

wherein $R_1$ is as defined for formula I and X is bromine or chlorine, is reacted with urea in the presence of a base and a catalytic amount of at least one palladium complex compound, wherein the palladium complex compound comprises at least one ferrocenyl-biphosphine ligand.

2. A process according to claim 1, wherein the palladium complex compound comprises di-tert-butyl-[1-[2-(dicyclohexylphosphinyl)ferrocenyl]ethyl]phosphine.

3. A process according to claim 1, wherein the palladium complex compound comprises racemic di-tert-butyl-[1-[2-(dicyclohexylphosphinyl)ferrocenyl]ethyl]phosphine.

4. A process according to claim 1, wherein the palladium complex compound is used in a ratio of from 1:10 000 to 1:10 relative to the compound of formula II.

5. A process according to claim 1, wherein the reaction is carried out in an inert solvent.

6. A process according to claim 1, wherein X is chlorine.

\* \* \* \* \*